United States Patent [19]

Grose et al.

[11] 4,061,724

[45] Dec. 6, 1977

[54] CRYSTALLINE SILICA

[75] Inventors: Robert William Grose, Mahopac; Edith Marie Flanigen, White Plains, both of N.Y.

[73] Assignee: Union Carbide Corporation, New York, N.Y.

[21] Appl. No.: 615,557

[22] Filed: Sept. 22, 1975

[51] Int. Cl.$^2$ .............................................. C01B 33/12
[52] U.S. Cl. .................................... 423/335; 423/339
[58] Field of Search ................................ 423/335, 339

[56] References Cited

U.S. PATENT DOCUMENTS 3,556,725  1/1971  Chiola et al. .......................... 423/339

FOREIGN PATENT DOCUMENTS 1,003,195  2/1957  Germany ............................. 423/339
927,658    5/1963  United Kingdom ................. 423/339

OTHER PUBLICATIONS

Merrill et al., "J. Phys. Chem.," 55, 187, (1951).

*Primary Examiner*—Jack Cooper
*Attorney, Agent, or Firm*—Richard G. Miller

[57] ABSTRACT

A novel crystalline silica composition having uniform pore dimensions of approximately 6 Angstrom units is prepared by calcining a crystalline hydrated alkylonium silicate prepared hydrothermally from a reaction mixture containing as essential reagents, water, amorphous silica and a quaternary ammonium compound at a pH of at least 10. The crystalline silica, because of its uniform pore structure, is capable of making size-selective separations of molecular species, but neither it nor its silicate precursor exhibit ion-exchange properties.

This absorbent has a very useful hydrophobic/organophilic characteristic which permits its use in selectively adsorbing organic materials from water, either in liquid or vapor phase.

2 Claims, No Drawings

CRYSTALLINE SILICA

The present invention relates in general to a novel crystalline silica composition and to the method for preparing same. More particularly it relates to a novel crystalline silica composition which exhibits molecular sieve properties characteristic of a number of crystalline aluminosilicate compositions but which exhibits none of the ion-exchange properties which are essential to the latter class of compositions commonly referred to as zeolitic molecular sieves.

Crystalline forms of silica are found in nature and also exist as synthetic forms which apparently have no natural counterpart. Among those found in nature are quartz, tridymite and cristobalite, each having polymorphic forms stable in different ranges of temperature. At ordinary temperatures the stable form is alpha-quartz which inverts at 573° C. to beta-quartz, which is stable up to 867° C. At this temperature level, tridymite becomes the stable phase and remains so up to 1470° C. At temperatures in excess of 1470° C. cristobalite is the stable phase and remains so up to about 1713° C.

What is alleged to be the first true silica polymorph synthesized by man is coesite silica. This crystalline composition is defined and its method of manufacture described in detail in U.S. Pat. No. 2,876,072 issued to L. Coes, Jr. on Mar. 3, 1959. It has also been proposed to prepare crystalline polysilicate by extracting aluminum from the tetrahedral framework of crystalline aluminosilicates of the molecular sieve type by means of treatment with steam, strong acids or organic chelating agents. The products are psuedomorphic after the precursor composition. A specific procedure of this kind is to be found in U.S. Pat. No. 3,506,400 issued to P. E. Eberly, Jr. et al. on Apr. 14, 1970. While the latter class of compositions presumably are composed only silica, they appear to remain as defect structures having the same quantity of silica per unit cell as their aluminosilicate precursors. In at least some instances in which aluminum is extracted from zeolitic frameworks, the extraction is reversible, and similar elements such as germanium can be inserted into the tetrahedral structure. In this regard see U.S. Pat. No. 3,640,681 issued Feb. 8, 1972 to P. E. Pickert.

The crystalline silica polymorph of the present invention, hereinafter denominated "silicalite" has in the as-synthesized form a specific gravity at 25° C. of 1.99 ± 0.05 g/cc as measured by water displacement. In the calcined (600° C in air for 1 hour) from silicalite has a specific gravity of 1.70 g ± 0.05 g/cc. With respect to the mean refractive index of silicalite crystals, values obtained by measurement of the as-synthesized form and the calcined form (600° C. in air for 1 hour) are, respectively, 1.48 ± 0.01 and 1.39 ± 0.01.

For comparison purposes, the foregoing values are presented in Table I along with values for refractive index and density for other forms of crystalline silica.

TABLE I

| DENSITY AND REFRACTIVE INDEX DATA FOR CRYSTALLINE SILICAS[1] | | |
|---|---|---|
| Silica | D | d, g/cc |
| Quartz | 1.553,1.544 | 2.66 |
| Tridymite | 1.469,1.473,1.47 | 2.30 |
| Cristobalite | 1.486 | 2.3 |
| Opal (amorphous) | 1.41 – 1.46 | 1.9 – 2.3 |
| Melanophlogite | 1.42 – 1.46 | 1.99 – 2.10 1.9 calculated for calcined, anhydrous melanophlogite |
| Keatite | 1.513,1.522 | 2.50 |
| Coesite | 1.59,1.60 | 2.93 |
| Stishovite | 1.799,1.826 | 4.3 |
| Vitreous Silica | 1.458 – 1.475 | — |
| Silicalite (as-synthesized) | 1.48 ± 0.01 | 1.99 ± 0.05 |
| Silicalite (calcined)-600° C. | 1.39 ± 0.01 | 1.70 ± 0.05 |

[1] Data from "The Microscopic Determination of the Nonopaque Minerals" 2nd Edition, Geological Survey Bulletin 848, E. S. Larsen and H. Berman, 1934, and "Dana's System of Mineralogy," 7th Ed., Clifford Frondel, 1962.

The X-ray powder diffraction pattern of silicalite (600° C. calcination in air for one hour) has as its six strongest lines (i.e. interplanar spacings) those set forth in Table A below, wherein "S" = strong and "VS" = very strong.

TABLE A

| d-A | Relative Intensity |
|---|---|
| 11.1 ± 0.2 | VS |
| 10.0 ± 0.2 | VS |
| 3.85 ± 0.07 | VS |
| 3.82 ± 0.07 | S |
| 3.76 ± 0.05 | S |
| 3.72 ± 0.05 | S |

The following Table B lists the data representing the X-ray powder diffraction pattern of a typical silicalite composition containing 51.9 moles of $SiO_2$ per mole of $(TPA)_2O$, prepared according to the method of the invention (calcined in air at 600° C. for 1 hour).

TABLE B

| d-A | Relative Intensity | d-A | Relative Intensity |
|---|---|---|---|
| 11.1 | 100 | 4.35 | 5 |
| 10.02 | 64 | 4.25 | 7 |
| 9.73 | 16 | 4.08 | 3 |
| 8.99 | 1 | 4.00 | 3 |
| 8.04 | 0.5 | 3.85 | 59 |
| 7.42 | 1 | 3.82 | 32 |
| 7.06 | 0.5 | 3.74 | 24 |
| 6.68 | 5 | 3.71 | 27 |
| 6.35 | 9 | 3.64 | 12 |
| 5.98 | 14 | 3.59 | 0.5 |
| 5.70 | 7 | 3.48 | 3 |
| 5.57 | 8 | 3.44 | 5 |
| 5.36 | 2 | 3.34 | 11 |
| 5.11 | 2 | 3.30 | 7 |
| 5.01 | 4 | 3.25 | 3 |
| 4.98 | 5 | 3.17 | 0.5 |
| 4.86 | 0.5 | 3.13 | 0.5 |
| 4.60 | 3 | 3.05 | 5 |
| 4.44 | 0.5 | 2.98 | 10 |

Crystals of silicalite in both the as-synthesized and calcined form are orthorhombic and having the following unit cell parameters: $a$ = 20.05 A, $b$ = 20.0 A, $c$ = 13.4 A, with an accuracy of ± 0.1 A on each of the above values.

The pore diameter of silicalite is about 6 Angstrom units and its pore volume is 0.18 cc./gram as determined by adsorption. Silicalite adsorbs neopentane (6.2 A kinetic diameter) slowly at ambient room temperature. The uniform pore structure imparts size-selective molecular sieve properties to the composition, and the pore size permits the separation of p-xylene from o-xylene, m-xylene and ethylbenzene. Separations of compounds having quaternary carbon atoms from those having carbon-to-carbon linkages of lower value are also possible using silicalite as a size-selective adsorbent. The adsorbent also has a very useful hydrophobic/organophilic characteristic which permits its use in selectively adsorbing organic materials from water, either liquid or vapor phase. Neither silicalite nor its silicate precursor exhibits ion exchange properties.

The above-mentioned lack of ion-exchange capability in the silica composition of this invention is highly advantageous. Some aluminosilicate zeolites can be treated in a manner which promotes a hydrophobic character and makes them possible candidates for selective removal of organics from waste water; however, if the hydrophobic aluminosilicate adsorbent contains residual cation-exchange capacity, this is detrimental to the adsorbent when in contact with waste water streams containing a source of cations. The fixation of these cations in such aluminosilicate adsorbent drastically changes its hydrophobic character and/or pore size. Silicalite, however, is not affected by the presence of cations in a waste water stream.

The separation process contemplated here comprises, in general terms, contacting an aqueous solution such as a wastewater influent containing an organic compound with silicalite, adsorbing at least a portion of the organic compound in the inner adsorption surfaces of the silicalite and thereafter recovering, optionally as an effluent stream, the treated aqueous solution.

The preparation of silicalite involves the hydrothermal crystallization of a reaction mixture comprising water, a source of silica and an alkylonium compound at a pH of 10 to 14 to form a hydrous crystalline precursor, and subsequently calcining that precursor to decompose alkylonium moieties present therein. The exact structural nature of the precursor is not known. The precursor exhibits no ion exchange properties and since it does not contain $AlO_4$- tetrahedra as essential framework constituents, the alkylonium compound is not required to provide cations, such as are found in aluminosilicate zeolites, to balance the negative electrovalence thereof.

It can be theorized, however, that the principal function of the alkylonium compound is to provide a template-like material which predisposes the arrangement of $SiO_4$ tetrahedra into the particular lattice form which characterizes the silicalite composition of the present invention. Although we do not wish to be bound by this theory, the observable properties of the precursor indicate that the alkylonium moiety is more properly considered as being merely occluded in the $SiO_4$ framework than as a structural constituent thereof.

The alkylonium cation is suitably supplied to the reaction system by a compound preferably soluble in the reaction mixture and which contains a quaternary cation generally expressed by the formula

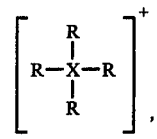

wherein R is an alkyl radical containing from 2 to 6 carbon atoms and X represents either phosphorus or nitrogen. Preferably R is ethyl, propyl or n-butyl, especially propyl, and X is nitrogen. Illustrative compounds include tetraethylammonium hydroxide, tetrapropylammonium hydroxide, tetrabutylammonium hydroxide, tetrabutylphosphonium hydroxide and the salts corresponding to the aforesaid hydroxides, particularly the chloride, iodide and bromide salts, for example, tetrapropylammonium bromide. The quaternary compounds can be supplied to the reaction mixture per se or can be generated in situ, such as by the reaction of tertiary amines with alkyl halides or sulfates.

When the quaternary cation is provided to the system in the form of the hydroxide in sufficient quantity to establish a basicity equivalent to the pH of 10 to 14, the reaction mixture need contain only water and a reactive form of silica as additional ingredients. In those cases in which the pH is required to be increased to above 10, ammonium hydroxide or alkali metal hydroxides can be suitably employed for that purpose, particularly the hydroxides of lithium, sodium or potassium. It has been found that not more than 6.5 moles of alkali metal oxide per mole-ion of quaternary cation is required for this purpose even if none of the quaternary cation is provided in the form of its hydroxide.

The source of silica in the reaction mixture can be wholly or in part alkali metal silicate but should not be employed in amounts greater than that which would change the molar ratio of alkali metal to quaternary cations set forth above. Other silica sources include solid reactive amorphous silica such as fume silica, silica sols and silica gel. Since the nature of the reaction system is favorable for the incorporation of alumina as an impurity into the crystalline silica product, care should be exercised in the selection of the silica source from the standpoint of its content of alumina as an impurity. Commercially available silica sols can typically contain from 500 to 700 ppm $Al_2O_3$, whereas fume silicas can contain from 80 to 2000 ppm of $Al_2O_3$ impurity. Small quantities of $Al_2O_3$ present in the silicalite product in no way significantly alter its essential properties, and in no sense is silicalite containing alumina or other oxide impurities properly considered to be a metallosilicate. The quantity of silica in the reaction system should be from about 13 to 50 moles $SiO_2$ per mole-ion of the quaternary cation. Water should be present in an amount of from 150 to 700 moles per mole-ion of the quaternary cation.

Accordingly, in preparing the crystalline silicalite precursor, there is formed a reaction mixture having a pH of at least 10 which in terms of moles of oxides contains from 150 to 700 moles $H_2O$, from 13 to 50 moles non-crystalline $SiO_2$ and from 0 to 6.5 moles $M_2O$, wherein M is an alkali metal, for each mole of $Q_2O$ present, wherein Q is a quaternary cation having the formula $R_4X^+$ in which each R represents hydrogen or an alkyl group containing from 2 to 6 carbon atoms and X is phosphorus or nitrogen.

The order in which the reagents are admixed is not a critical factor. The reaction mixture is maintained at a temperature of from about 100° to 250° C. under autogeneous pressure until crystals of the silicalite precursor are formed, ordinarily from about 50 to 150 hours. The crystalline product is recovered by any convenient means such as filtration. Advantageously the product is washed with water and can be dried in air at about 100° C.

When alkali metal hydroxide has been employed in the reaction mixture, alkali metal moieties appear as impurities in the crystalline product. Although the form in which these impurities exist in the crystalline mass has not yet been determined, they are not present as cations which undergo reversible exchange. The quaternary cation moiety is quite readily thermally decomposed and removed by calcination in an oxidizing atmosphere (air) or inert atmosphere at temperatures of from about 480° C. to 1000° C. The residual alkali metal in the product can be removed by washing with alkali metal halide solution or an aqueous acid solution of sufficient strength such as hydrochloric acid. The crystal structure is not otherwise affected by contact with strong mineral acids even at elevated temperatures due to the lack of acid-soluble constituents in its crystal structure.

The method for preparing silicalite and the nature of its chemical and physical properties are illustrated by the following examples:

EXAMPLE 1 a. A reaction mixture was prepared by dissolving 1.4 grams sodium hydroxide in 10 grams of water and adding the solution thus formed to 44 grams of an aqueous colloidal silica sol containing 30% by weight $SiO_2$. Thereafter a solution of 2.4 grams tetrapropylammonium bromide dissolved in 15 grams of water was added to form an overall reaction mixture containing 4.1 moles $Na_2O$, 50.0 moles $SiO_2$, 691 moles $H_2O$ per mole of tetrapropylammonium oxide. The synthesis mix was placed in a pressure vessel lined with an inert plastic material (polytetrafluoroethylene) and heated at 200° C. for 72 hours. The solid reaction product was recovered by filtration, washed with water and dried at 110° C. in air. The x-ray powder diffraction pattern of the silicalite precursor was quite similar to that which is exhibited by a class of aluminosilicate zeolite compositions commonly referred to as the "ZSM-5 family" even though they are distinctly different compositions. The significant lines of the latter materials are set forth in U.S. Pat. No. 3,728,408. Chemical analysis of the crystalline silica composition indicated the presence of 0.016 moles tetrapropylammonium (TPA) ion as $(TPA)_2O$; 0.011 moles $Na_2O$ and 0.8 moles $H_2O$ per mole of silica. Alumina impurity in the amount of about 650 ppm was also present.

b. A portion of the solid crystalline silica product obtained in part (a) supra was calcined in air at about 600° C. for 1 hour. After cooling to room temperature in the ambient atmosphere, the adsorption properties of the resulting silicalite was determined using a McBain-Bakr gravimetric adsorption system. In the system the sample was activated by heating to 350° C. under vacuum for 16 hours. Adsorption measurements made subsequently on a variety of adsorbates at various temperatures and a pressure of 750 torr produced the following data:

| Adsorbate | Kinetic Diam., A | Adsorption Temp., ° C. | Wt.-% Adsorbed |
|---|---|---|---|
| Oxygen | 3.46 | −183 | 13.7 |
| n-butane | 4.3 | 23 | 7.5 |
| $SF_6$ | 5.5 | 23 | 18.7 |
| Neopentane | 6.2 | 23 | 0.4 |

EXAMPLE 2

Using essentially the same procedure as in Example 1, 3 grams of tetrapropylammonium bromide, 25 grams of water, 44 grams of an aqueous colloidal silica sol (30 wt.-% $SiO_2$) and 2.3 grams of KOH were admixed to form a reaction mixture having a molar oxide ratio of:

$(TPA)_2O \cdot 3.25\ K_2O \cdot 40.0\ SiO_2 \cdot 560\ H_2O.$

The mixture was maintained at 200° C. for 72 hours, after which the crystalline product was isolated by filtration, washed with water and dried at 110° C. Portions of the product were submitted for X-ray and chemical analyses, which identified the product as silicalite. The chemical composition was, in terms of moles of oxides, $1.0\ (TPA)_2O \cdot 0.63\ K_2O \cdot 55.7\ SiO_2 \cdot 9.5\ H_2O.$ Alumina impurity in the amount of 591 ppm was also present.

EXAMPLE 3

Silicalite was prepared by dissolving 10.8 g. of $(C_3H_7)_4NBr$ in 20 g. of $H_2O$ and adding the solution to 158.4 g. of silica sol (30% $SiO_2$) with stirring. A solution of 10.2 g. of NaOH dissolved in 20 g. of $H_2O$ was then added to the synthesis mix with stirring. The synthesis molar oxide composition was:

$(TPA)_2O \cdot 6.2\ Na_2O \cdot 38.4\ SiO_2 \cdot 413\ H_2O.$

The synthesis mix was placed in two plastic-lined glass jars. One portion of the mix was heated at 100° C. for 72 hours and the other portion was heated at 100° C. for 144 hours. The solid reaction products were recovered by filtration, washed with $H_2O$, and dried at 110° C. Both products were identified as silicalite by X-ray and chemical analysis. The product crystallized for 72 hours had the following composition:

1.5 wt-% $Na_2O$, 7.7 wt-% C, 0.96 wt-% N, 82.5 wt-% $SiO_2$; 15.5 wt-% loss on ignition, 769 ppm $Al_2O_3$ impurity.

A portion of the 72-hour product was calcined at 600° C. for 2 hours in an air purge. One gram of the calcined product was added to 10 ml of 1.0 vol.% n-butanol in $H_2O$ solution and shaken. The absorbent selectively removed 98.8% of the n-butanol from the solution as indicated by gas chromatographic analysis of the treated solution. In another test demonstrating the selectivity of silicalite for organics over $H_2O$, a one-gram sample of the above calcined product was added to 10 ml of 0.1 wt-% phenol in $H_2O$ solution and shaken. The gas chromatographic analysis of the solution after contact with calcined silicalite revealed that the adsorbent removed 81% of the phenol from the solution.

In another test, this time demonstrating aromatic separation, a one-gram sample of the above calcined product was contacted with 10 ml. of 1.0 wt-% benzene in cyclohexane and shaken. The adsorbent removed 16.1 wt-% benzene from the solution as analyzed by gas chromatography.

EXAMPLE 4

A $(C_3H_7)_4NOH$ solution was prepared by dissolving 9.9 g. of $(C_3H_7)_4NBr$ in 25 g of $H_2O$ and adding 5.0 g of $Ag_2O$. After heating to about 80° C. the $(C_3H_7)_4NOH$ solution was separated from precipitated AgBr by filtration and added to 44 g of aqueous silica sol (30% $SiO_2$) with manual stirring. The synthesis molar oxide composition was:

$(TPA)_2O \cdot 13.3\ SiO_2 \cdot 184\ H_2O.$

The synthesis mix was placed in a polytetrafluoroethylene-lined pressure vessel and heated at about 200° C. and autogenous pressure for about 72 hours. The solid reaction product was recovered by filtration, washed with H₂O, and dried at 110° C. A portion of the solids was submitted for X-ray analysis and chemical analysis. The silicalite of the analyzed solids exhibited the characteristic physical properties hereinbefore described. The overall solids analyzed as 0.19 wt-% Na₂O, 8.1 wt-% carbon, 0.91 wt-% nitrogen, 87.4 wt-% SiO₂ and 1.5 wt-% H₂O. The trace amount of Na₂O is attributable to the silica sol reagent.

EXAMPLE 5

Silicalite was prepared by dissolving 9.0 g of (C₃H₇)₄NBr in 30 g of H₂O and adding the solution to 39.6 grams of fume silica slurried in 100 g of H₂O. A solution of 4.2 g of NaOH dissolved in 37 g of H₂O was then added to the synthesis mix with stirring. The synthesis molar oxide composition ratio was:

(TPA)₂O . 3.25 Na₂O . 40 SiO₂ . 552 H₂O.

The silicalite product obtained by crystallizing the synthesis mixture at 200° C. for 70 hours was found to contain only 155 ppm alumina as an occluded impurity.

EXAMPLE 6

Silicalite was prepared by dissolving 10.0 g of (C₄H₉)₄PCl in 50 g of H₂O and adding the solution to 44 g of aqueous colloidal silica sol (30 wt-% SiO₂) with stirring. A solution of 1.4 g of NaOH dissolved in 50 g of H₂O was then added with stirring to the synthesis mix. The synthesis molar oxide composition was:

(TBP)₂O . 1.08 Na₂O . 13.3 SiO₂ . 441 H₂O.

The synthesis mix was placed in a polytetrafluoroethylene-lined pressure vessel and heated at about 200° C. and autogenous pressure for 72 hours. The solid reaction product was recovered by filtration, washed with H₂O, and dried at 110° C. The crystalline product was identified as silicalite by its characteristics X-ray powder diffraction pattern and by chemical analysis, which gave the following composition:

0.6 wt-% Na₂O, 6.5 wt-% C, 1.1 wt-% P, 88.0 wt-% SiO₂, 2.4 wt-% H₂O.

The product molar oxide composition was:

(TBP)₂O . 0.58 Na₂O . 87.3 SiO₂ . 7.9 H₂O.

A sample of the product was calcined in air at about 600° C for one hour. The calcined sample was then placed in a McBain-Bakr gravimetric adsorption system and activated at 350° C under vacuum for about 16 hours. The activated sample adsorbed 14.1 wt-% O₂ -183° C and 750 torr, 7.7 wt-% n-butane, 21.1 wt-% SF₆, and 0.5 wt-% neopentane at 23° C and 750 torr.

EXAMPLE 7

Silicalite was prepared by dissolving 7.2 g of (C₂H₅)₄NBr in 15 g of H₂O and adding the solution to 44 g of aqueous silica sol (30 wt-% SiO₂) with stirring. A solution of 1.4 g of NaOh dissolved in 10 g of H₂O was then added with stirring to the synthesis mix. The synthesis molar oxide composition was:

(TEA)₂O . 1.08 Na₂O . 13.3 SiO₂ . 184 H₂O.

The synthesis mix was placed in a tetrafluoroethylene-lined pressure vessel and heated at about 200° C. and autogenous pressure for 72 hours. The solid reaction product was recovered by filtration, washed with H₂O, and dried at 110° C. The product was found to be silicalite.

EXAMPLE 8

A (C₃H₇)₄NOH solution was prepared by dissolving 13.5 g of (C₃H₇)₄NBr in 30 g H₂O and adding 7.5 g of Ag₂O. After heating to about 80° C, the (C₃H₇)₄NOH solution was separated from the precipitated AgBr by filtration and mixed with a slurry of 20.8 g of "Cab-O-Sil" fume silica in 54 g of H₂O. The synthesis molar oxide composition was:

(TPA)₂O . 13.3 SiO₂ . 184 H₂O

The synthesis mix was placed in a tetrafluoroethylene-lined pressure vessel and heated at about 200° C and autogenous pressure for about 72 hours. The solid reaction product was recovered by filtration, washed with H₂O, and dried at 110° C. A portion of the product was submitted for X-ray analysis and contained the d-values listed in Table A. Chemical analysis of the product gave the following composition: 8.7 wt.-% C, 0.81 wt.-% N, 87.3 wt.-% SiO₂, 1.0 wt.-% H₂O, 90 (± 30) ppm Al₂O₃, and less than 50 ppm Na₂O. The product structural molar oxide composition was:

(TPA)₂O . 48.2 SiO₂ . 1.8 H₂O.

Although no Na₂O or Al₂O₃ was deliberately added to the synthesis mix, the silica source does contain trace amounts of Al₂O₃ and Na₂O which was incorporated in the product. A sample of the product was calcined in air at about 600° C for 1 hour. The activated sample adsorbed 18.2 wt.-% O₂ at -183° C and 750 torr, 9.9 wt.-% n-butane, 26.6 wt.-% SF₆, and 0.5 wt.-% neopentane at 23° C and 750 torr.

EXAMPLE 9

10.9 g of (C₃H₇)₄NBr was dissolved in 30 g of H₂O and added to a slurry of 49.4 g of "Ucar" fume silica in 100 g of H₂O and 3 g NH₄OH. The synthesis molar oxide composition was:

(TPA)₂O . 1.3(NH₄)₂O . 40 SiO₂ . 365 H₂O.

The synthesis mix was placed in a tetrafluoroethylene-lined pressure vessel and heated at about 200° C for 95 hours. The solid reaction product was recovered by filtration, washed with H₂O, and dried at 110° C. A portion of the product was submitted for X-ray analysis; the resulting X-ray pattern was found to contain the d-values listed in Table A.

EXAMPLE 10

Samples of calcined silicalite prepared by the method of Example 1 (200° C synthesis, 600° C calcination) were stirred with aqueous solutions of HCl or NaCl as outlined below which removed residual alkali metal to the levels shown:

| Sample No. | Concentration of NaCl | HCl | Time (hrs.) | Temp. (° C) | Alkali Metal Contents wt.-% Na₂O before | after |
|---|---|---|---|---|---|---|
| 1 | — | 1N | 1 | 20 | 1.12 | 0.09 |
| 2 | — | 1N | 1 | 80–100 | 1.19 | <0.02 |

-continued

| Sample No. | Concentration of NaCl | Concentration of HCl | Time (hrs.) | Temp. (° C) | Alkali Metal Contents wt.-% Na$_2$O before | Alkali Metal Contents wt.-% Na$_2$O after |
|---|---|---|---|---|---|---|
| 3 | 5M | — | 1 | 80–100 | 1.1 | <0.02 |

The excellent stability of silicalite was illustrated by subsequent treatment of the essentially pure SiO$_2$ product derived from Sample No. 2 with 600° C steam at 1 atmosphere for 6 hours. The product still exhibited the characteristic unique properties of silicalite.

As additional illustration of the remarkable selectivity of the silicalite composition of the invention for organic materials over water, Table C containing Examples 11 to 13 is presented. The procedure employed is similar to that described in Example 3, above. A 1.0-gram sample of calcined (600° C) silicalite and 10.0 grams of the aqueous organic solution are placed in a serum bottle which is capped, shaken and allowed to equilibrate for at least 12 hours. A blank (same aqueous organic solution without adsorbent) is always used for comparison. Analysis of the treated solution is done by gas chromatography.

TABLE C

| Example No. | Silicalite Lot No. | Organic Component (O.C.) | % Concentration of O.C.* Start | % Concentration of O.C.* End | %O.C. Removal |
|---|---|---|---|---|---|
| 11 | 35–1 (a) | n-butanol | 1.0 bv | 0.008bv | 99.2 |
|  |  | methyl cellosolve | 1.0 bv | 0.282bv | 71.8 |
|  |  | methanol | 1.0 bv | 0.825bv | 17.5 |
|  |  | phenol | 0.1 bw | 0.021bw | 79 |
|  |  | SO$_2$ | 0.7 bw | 0.245bw | 64.9 |
| 12 | 66–2 (b) | n-butanol | 1.0 bv | 0.015bv | 98.5 |
|  |  | phenol | 0.1 bw | 0.020bw | 80. |
| 13 | ~48 (a) | n-butanol | 1.0 bv | 0.008bv | 99.2 |
|  |  | phenol | 0.1bw | 0.011bw | 89. |

*bv = % by volume; bw = % by wt.
(a) Synthesized at 200° C
(b) Synthesized at 100° C

EXAMPLE 14

In a procedure similar to that described in the last paragraph of Example 3 above, a 1-gram silicalite sample synthesized at 200° C and calcined at 600° C, was contacted with 10 ml. of a 1.0 wt.-% solution of benzene in cyclohexane. Gas chromatography analysis indicated that 23.8% of the benzene had been removed from the solution. These data indicate that silicalite is able to make separations despite very small differences in the size of adsorbate molecules.

The foregoing information on the separation capabilities of silicalite demonstrates that a variety of useful industrial processes employing this adsorbent are now made possible. As examples of organic components often found in various industrial or municipal waste streams, methanol, butanol, methyl cellosolve, phenol and sulfur dioxide are effectively separated from aqueous solutions containing such components.

The foregoing X-ray powder diffraction data were obtained by standard techniques. Thus the radiation was the K-alpha doublet of copper, and a Geiger-counter spectrometer with a strip-chart pen recorder was used. The peak or line heights and the positions thereof as a function of 2 times theta, where theta is the Bragg angle, were read from the spectrometer chart. From these the relative intensities of the reflected lines or peaks, and $d$, the interplanar spacing in Angstrom units corresponding to the recorded lines were determined.

What is claimed is:

1. A silica polymorph consisting of crystalline silica, said silica polymorph after calcination in air at 600° C for 1 hour, having a mean refractive index of 1.39 ± 0.01 and a specific gravity at 25° C of 1.70 ± 0.05 g./cc.

2. A silica polymorph consisting of crystalline silica, said silica polymorph after calcination in air at 600° C for 1 hour having as the six strongest d-values of its X-ray powder diffraction pattern those set forth in Table A.

* * * * *

Dedication 4,061,724.—*Robert William Grose,* Mahopac and *Edith Marie Flanigen,* White Plains, N.Y. CRYSTALLINE SILICA. Patent dated Dec. 6, 1977. Dedication filed Sept. 20, 1982, by the assignee, *Union Carbide Corp.*

Hereby dedicates to the Public the entire term of said patent.
[*Official Gazette November 16, 1982.*]